(12) United States Patent
Shen et al.

(10) Patent No.: US 12,249,008 B2
(45) Date of Patent: Mar. 11, 2025

(54) IMPLICIT NEURAL REPRESENTATION LEARNING WITH PRIOR EMBEDDING FOR SPARSELY SAMPLED IMAGE RECONSTRUCTION AND OTHER INVERSE PROBLEMS

(71) Applicant: The Board of Trustees of the Leland Stanford Junior University, Stanford, CA (US)

(72) Inventors: Liyue Shen, Cambridge, MA (US); Lei Xing, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 447 days.

(21) Appl. No.: 17/944,709

(22) Filed: Sep. 14, 2022

(65) Prior Publication Data
US 2023/0024401 A1 Jan. 26, 2023

Related U.S. Application Data

(63) Continuation-in-part of application No. 17/835,896, filed on Jun. 8, 2022, now abandoned.
(Continued)

(51) Int. Cl.
*G06N 3/08* (2023.01)
*G06T 11/00* (2006.01)

(52) U.S. Cl.
CPC ............. *G06T 11/006* (2013.01); *G06N 3/08* (2013.01); *G06T 11/005* (2013.01); *G06T 2210/41* (2013.01)

(58) Field of Classification Search
CPC . G06T 11/006; G06T 11/005; G06T 2210/41; G06T 2211/441; G06T 2211/436;
(Continued)

(56) References Cited

U.S. PATENT DOCUMENTS 11,808,832 B2 * 11/2023 Chatterjee ............ G06N 3/0455
2021/0177371 A1 * 6/2021 Wang ..................... A61B 90/39

OTHER PUBLICATIONS

Mildenhall, et al., "Nerf: Representing scenes as neural radiance fields for view synthesis," In European Conference on Computer Vision, pp. 405-421, 2020.
(Continued)

*Primary Examiner* — Charlotte M Baker
(74) *Attorney, Agent, or Firm* — LUMEN PATENT FIRM

(57) ABSTRACT

A method for diagnostic imaging reconstruction uses a prior image $x^{pr}$ from a scan of a subject to initialize parameters of a neural network which maps coordinates in image space to corresponding intensity values in the prior image. The parameters are initialized by minimizing an objective function representing a difference between intensity values of the prior image and predicted intensity values output from the neural network. The neural network is then trained using subsampled (sparse) measurements of the subject to learn a neural representation of a reconstructed image. The training includes minimizing an objective function representing a difference between the subsampled measurements and a forward model applied to predicted image intensity values output from the neural network. Image intensity values output from the trained neural network from coordinates in image space input to the trained neural network are computed to produce predicted image intensity values.

6 Claims, 9 Drawing Sheets

Related U.S. Application Data

(60) Provisional application No. 63/210,433, filed on Jun. 14, 2021.

(58) Field of Classification Search
CPC ........ G06N 3/08; G06N 3/048; G06N 3/0499; G06N 3/09; G16H 30/40; G16H 50/20
USPC ....................................................... 382/131
See application file for complete search history.

(56) References Cited

OTHER PUBLICATIONS

Sun, et al., "CoIL: Coordinate-based Internal Learning for Imaging Inverse Problems," arXiv preprint arXiv:2102.05181, 2021.

* cited by examiner

ABSTRACT# IMPLICIT NEURAL REPRESENTATION LEARNING WITH PRIOR EMBEDDING FOR SPARSELY SAMPLED IMAGE RECONSTRUCTION AND OTHER INVERSE PROBLEMS

CROSS-REFERENCE TO RELATED APPLICATIONS

This application is a continuation-in-part of U.S. patent application Ser. No. 17/835,896 filed Jun. 8, 2022, which claims priority from U.S. Provisional Patent Application 63/210,433 filed Jun. 14, 2021, both of which are incorporated herein by reference.

STATEMENT OF FEDERALLY SPONSORED RESEARCH

This invention was made with Government support under contract CA256890 awarded by the National Institutes of Health, and under contract CA227713 awarded by the National Institutes of Health. The Government has certain rights in the invention.

FIELD OF THE INVENTION

The present invention relates generally to diagnostic imaging. More specifically, it relates to methods for image reconstruction in computed tomography and magnetic resonance imaging.

BACKGROUND OF THE INVENTION

Image reconstruction is an inverse problem that solves for a computational image based on sampled sensor measurements. When the sampled measurements are sparse, it becomes challenging to perform image reconstruction due to limited information in the measurement data from which to reconstruct an image.

Although the advantages of deep learning models for medical image reconstruction are well known, there are increasing concerns regarding the limitations of the current deep learning approaches. First, training deep neural networks is data-intensive and requires large-scale datasets. This may prevent many practical applications due to the difficulty of data collection. The limited availability of specific image modalities or images of rare diseases may make it difficult to acquire sufficient training data for deep learning modeling. In addition, there is a common concern about the robustness and reliability of deep reconstructed images. For example, recent study finds that the small but significant structural changes in tumors or lesions may not be accurately captured in the deep reconstructed images. Finally, the generalization capability of deep networks is unclear. The trained deep networks may produce poor performance when generalized to data out of the training distribution, such as across different imaging modalities or across different anatomical sites. The model generalizability is related to not only the training data distribution but also the network structure. For example, it is a non-trivial task to directly transfer a deep network developed for MRI reconstruction to the task of CT reconstruction due to different sensor measurements fields. Because of these issues and limitations, new insights are needed in developing deep learning-based image reconstruction methods.

SUMMARY OF THE INVENTION

In this work, we propose an implicit Neural Representation learning methodology with Prior embedding (NeRP) to reconstruct a computational image from sparsely sampled measurements. The method differs fundamentally from previous deep learning-based image reconstruction approaches in that NeRP exploits the internal information in an image prior, and the physics of the sparsely sampled measurements to produce a representation of the image. No large-scale data is required to train the NeRP except for a prior image and sparsely sampled measurements. In addition, we demonstrate that NeRP is a general methodology that generalizes to different imaging modalities such as CT and MRI. We also show that NeRP can robustly capture the subtle yet significant image changes required for assessing tumor progression.

In conventional deep-learning-based image reconstruction, a neural network is trained to learn the mapping from the sampled measurement data to the reconstructed images using a large-scale training database of fully sampled measurements and corresponding reconstructed ground truth images. In contrast, the present approach learns the network itself, i.e. multi-layer perceptron (MLP), to map the image spatial coordinates to the corresponding intensity values. Using a prior image and sparse measurement data of a subject, neural network learns the continuous implicit neural representation of the entire image by encoding the full image spatial field into the weights of MLP model. Image reconstruction is then reduced to simply querying the model embedded in the network.

This deep learning methodology for medical image reconstruction from sparsely sampled measurements follows a unique approach of learning the implicit neural representation of image with prior embedding (NeRP). The method requires no training data from external subjects and can be easily generalized across different imaging modalities and different anatomical sites. Applications include: (1) Tomographic imaging with sparsely sampling to significantly speed up data acquisition and/or reduce the potential radiation side effects. (2) Magnetic resonance imaging from under-sampled k-space for accelerated acquisition and reconstruction. (3) Simplified hardware design with substantially reduced efforts in data acquisition. (4) Other imaging modalities and devices/systems that can be formulated as an inverse problem.

The present NeRP method provides a new perspective to the problems of image reconstruction, which promises to overcome the shortcomings of previous deep reconstruction approaches. First, NeRP requires no large training data from external subjects; it only requires sparsely sampled sensor measurements of the subject and a prior image from a previous scan of the same subject. In addition, from our experiments, the reconstructed images from NeRP are more robust and reliable, and can capture the small structural changes such as tumor or lesion progression. The implicit image priors captured by network structure and the prior embedding can effectively incorporate the prior knowledge in the reconstruction process, which makes it possible for the network to capture and reconstruct the fine structural details in the resultant images. As a result of the previous two points, NeRP can be more easily generalized to different image modalities, different anatomical sites, and different dimensionalities in the image reconstruction task. The relaxed requirements for training data make the method more transferrable and applicable across various applications. NeRP is a general methodology for medical image reconstruction with promising advantages over mapping-learning-based deep reconstruction methods.

Beyond image reconstruction, the method can be extended to solve other inverse problems with measurements (or sparse measurements) acquired at different time points or under different environments/conditions. Broadly, the method is able to tackle problems with spatial coordinate-dependence, such as dose (or other physical quantities such as wave, heat, magnetic field, sound waves, and so forth) distribution prediction, semantic segmentation, and cross-modality image translation. In these cases, the output of MLP network would be corresponding values with semantics in different contexts. Additionally, the method has potential to deal with the longitudinal problems, where the time dimension will be added as another dimension in the input of MLP network. In this way, both the temporal and spatial information and correlation are embedded into network parameters through neural representation learning, which can then be used for solving the longitudinal problems in clinical protocol to reveal quantities such as tumor progression and image content changes.

In one aspect, the invention provides a method for diagnostic imaging reconstruction. A prior image $x^{pr}$ from a scan of a subject is stored. The image has image intensity at each coordinate in image space. Parameters of a neural network are initialized using the prior image $x^{pr}$. The neural network maps coordinates in image space to corresponding intensity values in the prior image. The parameters are initialized by minimizing an objective function representing a difference between intensity values of the prior image and predicted intensity values output from the neural network, thereby creating an implicit neural representation of the prior image. A scan to acquire subsampled (sparse) measurements y of the subject is performed. The neural network is then trained using the measurements y to learn a neural representation of a reconstructed image x. The training includes minimizing an objective function representing a difference between the measurements y and a forward model applied to predicted image intensity values output from the neural network. Finally, image intensity values output from the trained neural network from coordinates in image space input to the trained neural network are computed to produce predicted image intensity values.

Preferably, Fourier feature mapping is used to transform spatial coordinates to encoded coordinates prior to input to the neural network. The neural network is preferably implemented by a deep fully-connected network or multi-layer perceptron (MLP). The MLP preferably uses periodic activation functions after each fully-connected layer.

BRIEF DESCRIPTION OF THE DRAWINGS

FIG. 1A illustrates a conventional deep neural network that learns the mapping from the sensor (measurements) domain to image domain. FIG. 1B illustrates a deep neural network that learns the implicit neural representation of the reconstructed image, according to an embodiment of the invention.

DETAILED DESCRIPTION OF THE INVENTION

Image reconstruction is conventionally formulated as an inverse problem, with the goal of obtaining the computational image of a subject from measured sensor data. For example, projection data are measured for computed tomography imaging (CT) while frequency domain (k-space) data are sampled for magnetic resonance imaging (MRI). To reconstruct artifact-free images, dense sampling in measurement space is required to satisfy the Shannon-Nyquist theorem. However, in many practical applications it would be desirable to reconstruct images from sparsely sampled data. One important application is reducing radiation dose in CT imaging. Another application is accelerating MRI acquisition time. The ill-posed nature of the sparse sampling image reconstruction problem poses a major challenge for algorithm development.

Figure 1:
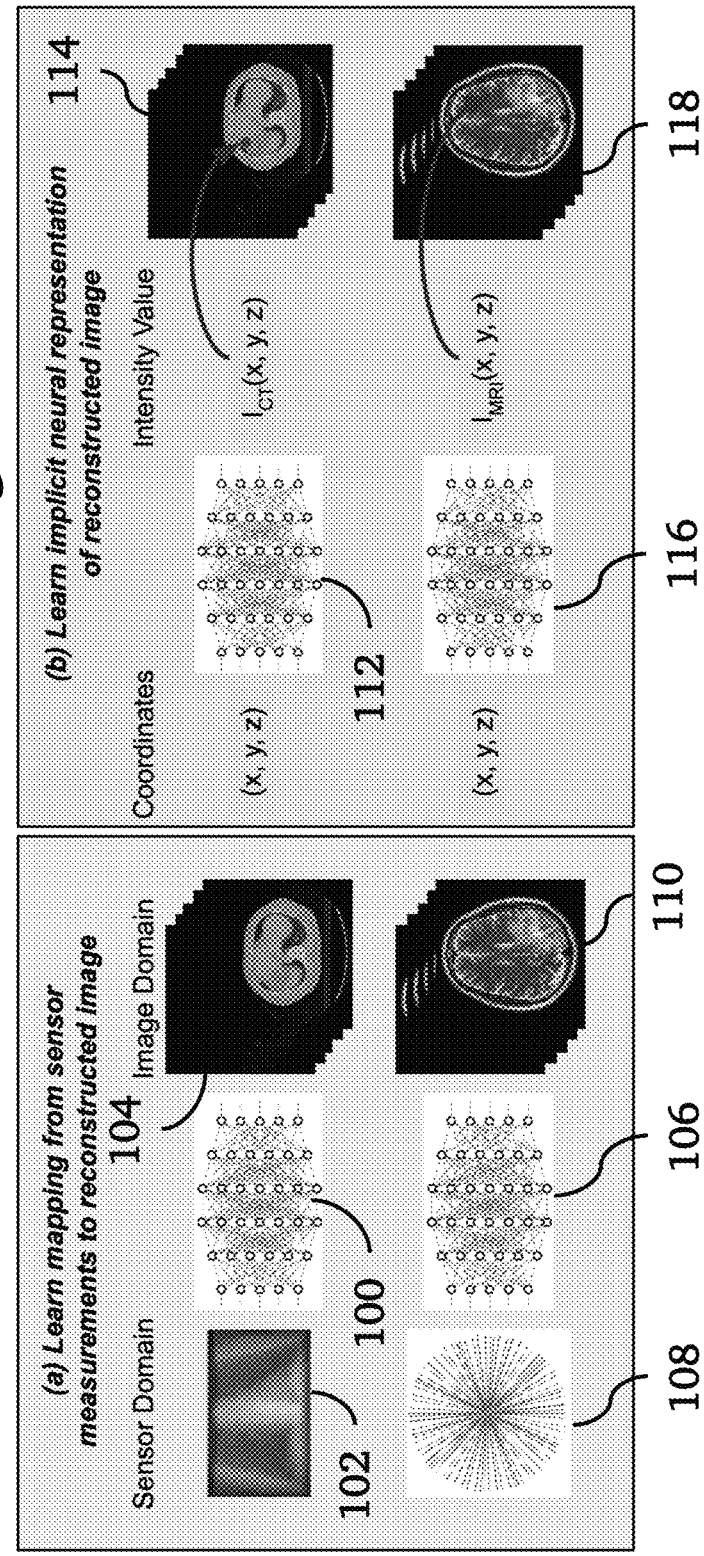
FIGS. 1A-1B are schematic illustrations comparing different approaches for deep learning-based medical image reconstruction.

With the unprecedented advances in deep learning, deep neural networks driven by learning from large-scale data have achieved impressive progress in many fields including computational image reconstruction. Many research works have introduced deep learning models for medical imaging modalities such as CT and MRI. The key to these deep learning approaches is training convolutional neural networks (CNNs) to learn the mapping from raw measurement data to the reconstructed image by exploiting the large-scale training data. FIG. 1A provides a schematic illustration of conventional approaches for deep learning-based medical image reconstruction. In the top row illustrating CT image reconstruction, a deep neural network 100 is trained to learn the mapping from the sensor (measurements) domain 102 (i.e., projection space data) to image domain 104. In the bottom row illustrating MRI image reconstruction, a deep neural network 106 is trained to learn the mapping from the sensor measurements domain 108 (i.e., frequency space data) to image domain 110. In both cases, the network maps sensor data to image data and learns the hidden transformation information embedded in the data through the data-driven training procedure.

These conventional deep learning reconstruction methods, however, have some limitations. For example, the acquisition of large-scale training data sets can be a bottleneck, the reconstructions may not be robust when deployed to unseen subjects, the reconstructions can be unstable with subtle yet significant structural changes such as tumor growth, and there can also be difficulties generalizing to different image modalities or anatomical sites.

Here we introduce an entirely new paradigm for image reconstruction that overcomes many of the disadvantages of existing methods. We introduce a method that learns the implicit neural representation of an image with prior embedding (herein called "NeRP"). This is an essentially different perspective from previous deep learning-based reconstruction methods.

A schematic overview of the NeRP method is illustrated in FIG. 113. In the case of CT image reconstruction, a deep neural network 112 is trained to learn the implicit neural representation of the reconstructed image 114. The input to the network 112 is the spatial coordinates for any points within the image field, while the output is the corresponding intensity values of the CT image 114. Similarly, in the case of MRI image reconstruction, a deep neural network 116 is trained to learn the implicit neural representation of the reconstructed image 118. The input to the network 116 is the spatial coordinates for any points within the image field, while the output is the corresponding intensity values of the CT image 118. Any image (e.g. CT, MRI) can be implicitly represented by a continuous function which is encoded into the neural network's parameters.

In contrast with conventional deep learning techniques in which a neural network is trained to learn the mapping from the sampled measurement data to reconstructed images based on a large-scale training database, this NeRP method learns the network, i.e., the multi-layer perceptron (MLP), to map the image spatial coordinates to the corresponding intensity values. The neural network learns the continuous implicit neural representation of the entire image by encoding the full image spatial field into the weights of MLP model. Image reconstruction is then reduced to simply querying the model embedded in the trained network. The image reconstruction problem is transformed into a network optimization problem. Instead of searching for the best match in the image space, we reconstruct the image by searching for it in the space of networks' weights. The MLP is trained by matching the subsampled measurements in raw data space (e.g., projection space sampling for CT or frequency space sampling for MRI), then integrating the forward model of the corresponding imaging system. For sparse sampling, the measurements alone may not provide sufficient information to precisely reconstruct images of the subject due to the ill-posed nature of the inverse problem. Accordingly, the NeRP framework exploits prior knowledge from a previous image for the same subject. This is particularly applicable to clinical protocols where patients are scanned serially over time, such as monitoring tumor response to therapy. The implicit neural representation first embeds the internal information of the prior image of the subject into the weights of MLP. This serves as the initialization for the search for the representation of the target image. Starting from this prior-embedded initialization, the network can be optimized to reach an optimal point in the function space given only sparsely sampled measurements from the same subject. Finally, the learned MLP generates the image reconstruction by traversing all the spatial coordinates in the image space. Note that NeRP requires no training data from external subjects; it only uses the sparsely sampled measurements of the subject and a prior image of the subject.

In NeRP, beyond leveraging image priors through optimization in the function space of network's parameters, we also take advantage of another image prior unique in medical domain. In medical imaging, it is common that one patient may have multiple imaging scans over time for the purpose of treatment assessment, or for image-guided interventions. Although the images are taken at different subject states, earlier scanned images can still provide useful prior knowledge of the patient anatomy. The neural representation method of NeRP provides a simple yet effective way to embed this prior information and facilitate the reconstruction of target image.

Figure 2:
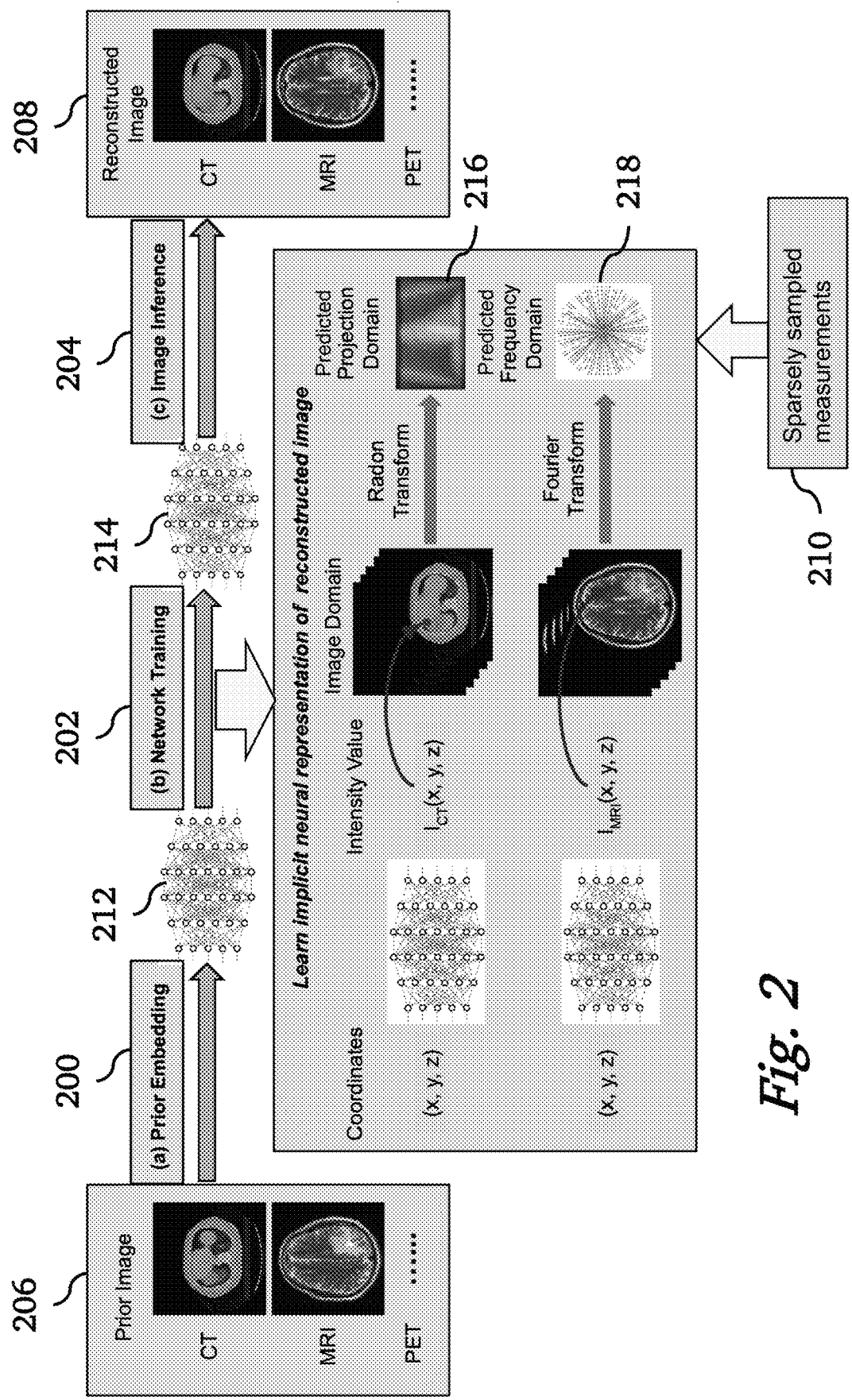
FIG. 2 is a schematic diagram of a processing pipeline for the framework of implicit neural representation learning with prior embedding (NeRP) for image reconstruction, according to an embodiment of the invention.

FIG. 2 is a schematic overview of the framework of implicit neural representation learning with prior embedding (NeRP) for image reconstruction. NeRP includes three steps to obtain from a prior image 206 and sparsely sampled measurements 210 the final reconstruction images 208: prior embedding 200, network training 202, and image inference 204.

In the prior embedding step 200, a prior image 206 from earlier scan of the same subject is embedded into the parameters of a neural network 212 as the implicit neural representation by training with coordinate-intensity pairs of the image 206 to encode the entire spatial image field into the network's parameters. Specifically, the network 212 is optimized in the training to seek the continuous function that precisely maps the spatial coordinates to corresponding intensity values of the prior image 206. After this step is completed, the network is initialized for subsequent training with the sparse measurement data.

In the network training step 202, using the prior-embedded network 202 as an initialization, the network is further trained based on the sparse samples in sensor (measurement) domain 210 (e.g., projection domain for CT imaging, frequency domain for MRI imaging). This training involves comparing the predicted projection/frequency domain data 216, 218 with the sparsely sampled measurements 210. The result of this network training is to produce a network 214 that has learned the neural representation of the target reconstruction image 208 from the subsampled measurements 210 of an the same subject, without using any ground truth images. Specifically, the differentiable forward model corresponding to the imaging system (e.g., Radon transform for CT imaging or Fourier transform for MRI imaging) is integrated to bridge the image space and sensor space. In this way, the trained network 214 is optimized in the continuous function space of the network's parameters, with the constraints of the subsampled measurements from the subject.

In the image inference step 204, the reconstructed image 208 is obtained using the trained network to infer image intensity values from the spatial coordinates across the image field.

The above steps will now be described in more detail below.

Problem Formulation

First, we mathematically formulate the inverse problem for computational image reconstruction. The forward process of imaging system can be modeled as:

$$y = Ax + e \quad (1)$$

where x is the desired image of the subject while y is the sampled sensor measurements. Matrix A represents the forward model of the imaging system, and e is the acquisition noise.

Image reconstruction aims to recover the computational image x of the subject, given the measurements y from sensors. In the problem of sparsely sampled image reconstruction, the measurements y are undersampled in sensor space due to either acceleration acquisition, as in MRI, or reduction of radiation, as in CT. The inverse problem for sparse sampling is ill-posed, and is typically formulated as an optimization problem with regularization:

$$x^* = \underset{x}{\mathrm{argmin}}\ \varepsilon(Ax, y) + \rho(x) \quad (2)$$

where $\varepsilon(Ax, y)$ is the data term, which measures the errors between Ax and y and guarantees the data consistency to sensor measurements. Function $\varepsilon$ can be different distance metrics such as L1 or L2 norm. $\rho(x)$ is the regularizer term characterizing the generic image prior. The regularizer $\rho(x)$ can be determined in many different ways to capture the various image characteristics, such as total variation of the image to enforce smoothness, or sparsity in a transform domain as in compressed sensing.

Neural Representation for Image

In implicit neural representation learning, the image is represented by a neural network as a continuous function. The network $\mathcal{M}_\theta$ with parameters $\theta$ can be defined as:

$$\mathcal{M}_\theta : c \to v \text{ with } c \in [0,1)^n, v \in \mathbb{R} \quad (3)$$

where the input c is the normalized coordinate index in the image spatial field, and the output v is the corresponding intensity value in the image. The network function $\mathcal{M}_\theta$ maps coordinates to the image intensities, which actually encodes the internal information of entire image into the network parameters. Thus, network structure $\mathcal{M}_\theta$ with the parameters $\theta$ is also regarded as the neural representation for the image. Note that, theoretically, a random image in any modality or in any dimension $x \in \mathbb{R}^n$ can be parameterized by the network using this method. Below we introduce the specific network structure used in our method.

Fourier Feature Embedding

Since Fourier features are shown to be effective for networks to learn high-frequency functions, we use a Fourier feature mapping $\gamma$ to encode the input coordinates c before applying them to the coordinate-based network. Thus, the encoded coordinates are:

$$\gamma(c) = [\cos(2\pi Bc), \sin(2\pi Bc)]^T \quad (4)$$

where matrix B represents the coefficients for Fourier feature transformation. Entries of matrix B are sampled from Gaussian distribution $\mathcal{N}(0, \sigma^2)$, where $\sigma$ is a hyperparameter characterizing the standard deviation of the prior distribution. After the Fourier feature embedding, the input to the network $\mathcal{M}_\theta$ is the encoded coordinates $\gamma(c)$.

Multi-Layer Perceptron Network

The network $\mathcal{M}_\theta$ is implemented by a deep fully-connected network, or multi-layer perceptron (MLP). The coordinate-based MLP parameterizes the continuous function to represent the entire image. This function is defined by the network structure as well as the network parameters. In the next section, we will describe in detail how to obtain the network parameters through optimization. For the network structure, the model depth and width of MLP are hyperparameters, characterizing the representative capability of the MLP model. Moreover, we use the periodic activation functions in our MLP model after each fully-connected layer, which are demonstrated to effectively represent fine details in signals.

NeRP for Sparsely Sampled Image Reconstruction

Next, we introduce how the implicit neural representation learning with prior embedding (NeRP) is used to solve image reconstruction problem. The goal is to recover the image x of the target subject, given corresponding sparsely sampled measurements y and a prior image $x^{pr}$. Note that $x^{pr}$ and x are different scans for the same subject, but at different time points. These capture the changing state of the subject, e.g., such as the tumor progression for monitoring patient response to therapy.

Prior Embedding

In the first step, we embed the prior image $x^{pr}$ into the network. We use the coordinate-based MLP $\mathcal{M}_\phi$ to map the spatial coordinates to corresponding intensity values in prior image $x^{pr}$. That is, $\mathcal{M}_\phi : c_i \to x_i^{pr}$, where i denotes the coordinate index in image spatial field. Given all the coordinate-intensity pairs in prior image $$\{c_i, x_i^{pr}\}_{i=1}^N$$

with a total of N pixels in the image, the randomly-initialized MLP is optimized based on the objective:

$$\phi^* = \arg\min_\phi \frac{1}{N} \sum_{i=1}^N \|\mathcal{M}_\phi(c_i) - x_i^{pr}\|_2^2 \quad (5)$$

After optimization, the internal information of prior image $x^{pr}$ is encoded into the MLP network $\mathcal{M}_{\phi^*}$ with the corresponding network parameters $\phi^*$. For clarity, we use $\mathcal{M}^{pr}$ to denote the prior-embedded MLP network, i.e. $x^{pr} = \mathcal{M}_{\phi^*} = \mathcal{M}^{pr}$.

Network Training

Given the prior-embedded MLP $\mathcal{M}^{pr}$ and measurements y, we further train the network using sparse measurement data to learn the neural representation of the target image. Based on the formulation in Eq. (2), the desire target image x is parametrized by a coordinate-based MLP $\mathcal{M}_\theta$ with parameters $\theta$. Thus, the data term is defined as $$\min_x \varepsilon(Ax, y) = \min_\theta \varepsilon(A\mathcal{M}_\theta, y),$$

where the optimization in image space is transformed to the optimization in the space of MLP's parameters. Furthermore, the regularizer $\rho(x)$ is replaced by the implicit image priors from network parametrization, including the internal information from prior image embedded in $\mathcal{M}^{pr}$ as well as the low-level image statistics prior captured by network structure itself $\mathcal{M}_\theta$. Thus, the optimization subjection in Eq. (2) can be formulated as follows:

$$\theta^* = \arg\min_\theta \varepsilon(A\mathcal{M}_\theta, y; \mathcal{M}^{pr}), \quad x^* = \mathcal{M}_{\theta^*} \quad (6)$$

The network $\mathcal{M}_\theta$ is trained by minimizing the L2-norm loss, which is initialized by the prior-embedded network $\mathcal{M}^{pr}$.

$$\theta^* = \arg\min_\theta \|A\mathcal{M}_\theta - y\|_2^2, \quad x^* = \mathcal{M}_{\theta^*} \quad (7)$$

Note that forward model A is adapted to the corresponding imaging system, such as Radon transform for CT imaging and Fourier transform for MRI imaging. The operation A is differentiable, which enables training the network $\mathcal{M}_\theta$ in an end-to-end fashion.

Image Inference

Finally, after the network is well trained, the reconstruction image can be generated by inferring the trained network across all the spatial coordinates in the image field. That is: $x^* : \{c_i, \mathcal{M}_{\theta^*}(c_i)\}_{i=1}^N$, where i denotes the coordinate index in image spatial field. This is denoted in short as $x^* = \mathcal{M}_{\theta^*}$ in Eqs. (6) and (7). Filling the intensity values at all the coordinates in image grid constitutes the final reconstruction image x*.

Technical Details of NeRP

In our implementation, we construct an 8-layer MLP network with a width of 256 neural nodes for CT reconstruction, where each fully-connected layer is followed by the periodic activation function except for the last layer. For MRI reconstruction, we increase the MLP width to 512 layers. We will discuss and analyze the influence of different network structures below. The Fourier feature embedding size is 256, where the hyper-parameter for the standard deviation of the coefficient's Gaussian distribution is set as 3 for MRI reconstruction and 4 for CT reconstruction. For prior embedding, the training objective in Eq. (5) is optimized by the Adam optimizer with a learning rate of 0.0001. The total training iterations are 1000 for 2D images and 2000 for 3D images. Next, given the prior-embedded MLP as the initialization, the reconstruction network is trained by optimizing the objective in Eq. (7) using the Adam optimizer with a learning rate of 0.00001. Usually we train 1000 iterations for 2D images and 2000 iterations for 3D images. We implemented our networks using PyTorch. For the differentiable forward model A, the Radon transform or forward projection operation for CT imaging is realized by using Operator Discretization Library (ODL). The non-uniform Fast Fourier Transform (NUFFT) for MRI imaging is implemented based on the torchkbnufft package.

Experiments and Results

To evaluate the NeRP method, we conducted experiments for 2D/3D CT and MRI image reconstruction with sparse sampling. For CT image reconstruction we assume 20 projections equally distributed across a semi-circle. We compute parallel-beam projections for 2D CT and cone-beam projections for 3D CT. For MRI image reconstruction, 40 radial spokes are sampled in k-space with golden angle as the angular interval. Beyond sparsely-sampled measurements data, a prior image from an earlier scan is also given. Since the prior image and reconstruction image are of the same patient at different time points, the prior image can provide useful information about the patient's anatomic structure while still allowing crucial structural and functional differences such as tumor or lesion changes. We will show the experimental results applying NeRP for 2D/3D CT and MRI image reconstruction with various image modalities and at various anatomical sites.

Datasets

Pancreas 4D CT Data

For CT image reconstruction, we collected a pancreas 4D CT data from a clinical patient. The 4D CT data is a temporal scan with a sequential series of 3D CT images over a respiratory cycle. Due to respiratory motion there is continuous motion in the CT images at different time points. In the first row of FIG. 3, we show the cross-sectional images at the same location from the 10 phases (time-points) of the CT images in the 4D CT. The continuous structural changes can be observed over the 10 temporal phases. In the experiments we use phase 1 as the prior image to reconstruct the CT images at the subsequent phases.

Head and Neck CT and Lung CT Data

To further validate the generalization of the NeRP method, we collected two clinical patient cases including a head and neck CT case and a lung CT case. For each case there are two longitudinal 3D CT images scanned for the same patient at time points during treatment with radiation therapy. The goal is to follow tumor volume to assess response to therapy. In the data preprocessing, we firstly conduct rigid image registration to align the two CT images at the same position. Then, we use NeRP to reconstruct the latter 3D CT image while using the earlier 3D CT image as the prior image.

Brain Tumor Progression MRI Data

For MRI image reconstruction we conducted experiments on a public dataset for brain tumor progression [29] [30]. This dataset includes MRI images from 20 subjects with primary newly diagnosed glioblastoma. The patients were treated with surgery and standard concomitant chemo-radiation therapy (CRT) followed by adjuvant chemotherapy [30]. For each patient, there are two MRI exams included, which were within 90 days following CRT completion and at tumor progression. Thus, the tumor changes can be clearly observed by comparing the two MRI exams of the same patient at different time points. In addition, each MRI exam contains multi-modality MRI images including T1-weighted, and contrast-enhanced T1-weighted (T1c), T2-weighted, FLAIR. In our experimental setting, we set the first MRI exam as the prior image and aim to reconstruct the MRI image in the second exam. This is tested for different MR image modalities respectively.

Experiments on 2D CT Image Reconstruction

Figure 3:
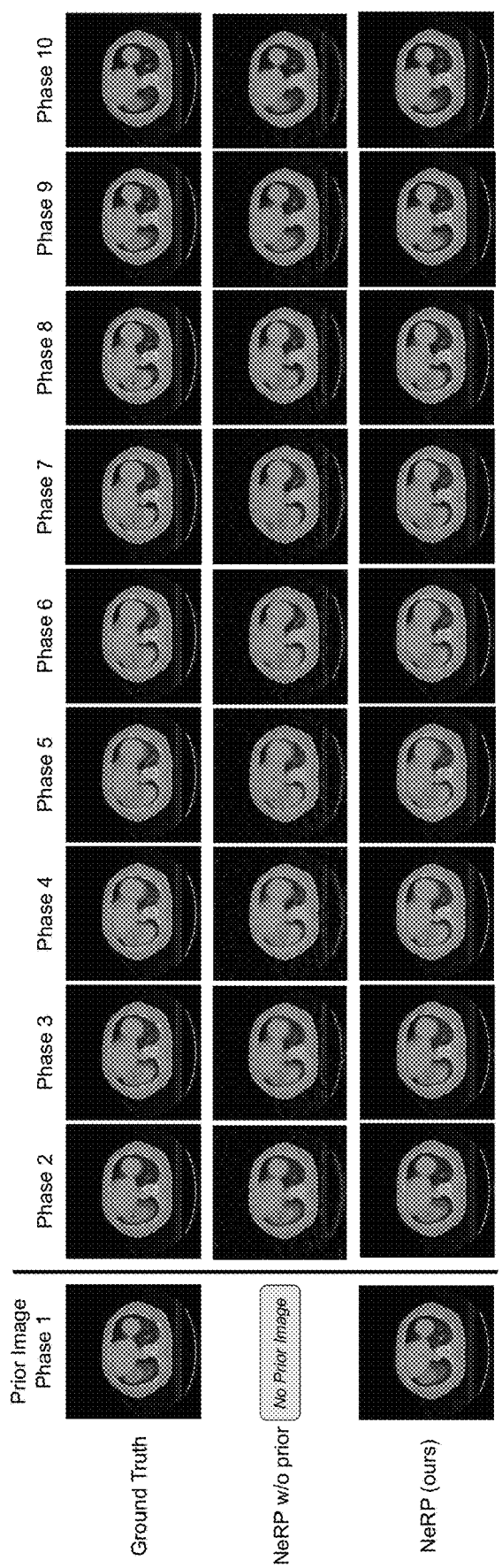
FIG. 3 is an image grid showing results of 2D CT image reconstruction for pancreas 4D CT data using 20 projections, according to an embodiment of the invention.

In FIG. 3, we show the 2D CT reconstruction results for pancreas 4D CT data using 20 projections for phase 2 to phase 10 using the NeRP method by using phase 1 as prior image. Note that 2D CT images are the cross-sectional slices at the same location extracted from the corresponding 3D CT images at each phase. After pre-processing, 2D CT images are all resized to 256×256. The first row shows the ground truth cross-sectional 2D slices at the same location over 10 phases in the pancreas 4D CT, where each column demonstrates one phase respectively. For comparison, we demonstrate reconstruction results for "NeRP w/o prior", where no prior image is used and the network is randomly initialized for training. From the results, we can see that NeRP can reconstruct high-quality images with clear anatomic structures, sharp organ boundary and high-contrast soft tissue and bones. More importantly, the reconstructed images can precisely capture the continuous changes with fine details over different phases, although the same prior image is used and only sparse projections are sampled for reconstructing the target image in each phase. By comparing to the results of "NeRP w/o prior", we see prior image embedding benefits reconstruction results in all phases with increased image sharpness and reduced noise. Therefore, we conclude that the prior embedding can provide useful prior knowledge that is critical to precisely reconstruct high-quality 2D CT images with sparse sampling. Moreover, we see that the NeRP method can reconstruct reliable images that precisely capture the small structural changes in the patient's anatomy. The final row shows the reconstruction images at different phases respectively by using the NeRP method, where the phase-1 image is used as the prior image for reconstructing the images in phase 2~10. For comparison, the second row shows the reconstruction results without using the prior embedding.

Experiments on 3D CT Image Reconstruction

To evaluate the effectiveness of NeRP in a higher-dimensional reconstruction task, we conducted experiments for 3D CT image reconstruction. In the first experiment on the pancreas 4D CT data, we use the entire phase-1 3D CT as the prior image and aim at reconstructing the 3D CT image at phase 6 with image size of 128×128×40 after image cropping and resizing. Note that phase 1 and phase 6 are exactly the inhale and exhale phases during this 4D CT scan, which have the largest structural difference.

Figure 4:
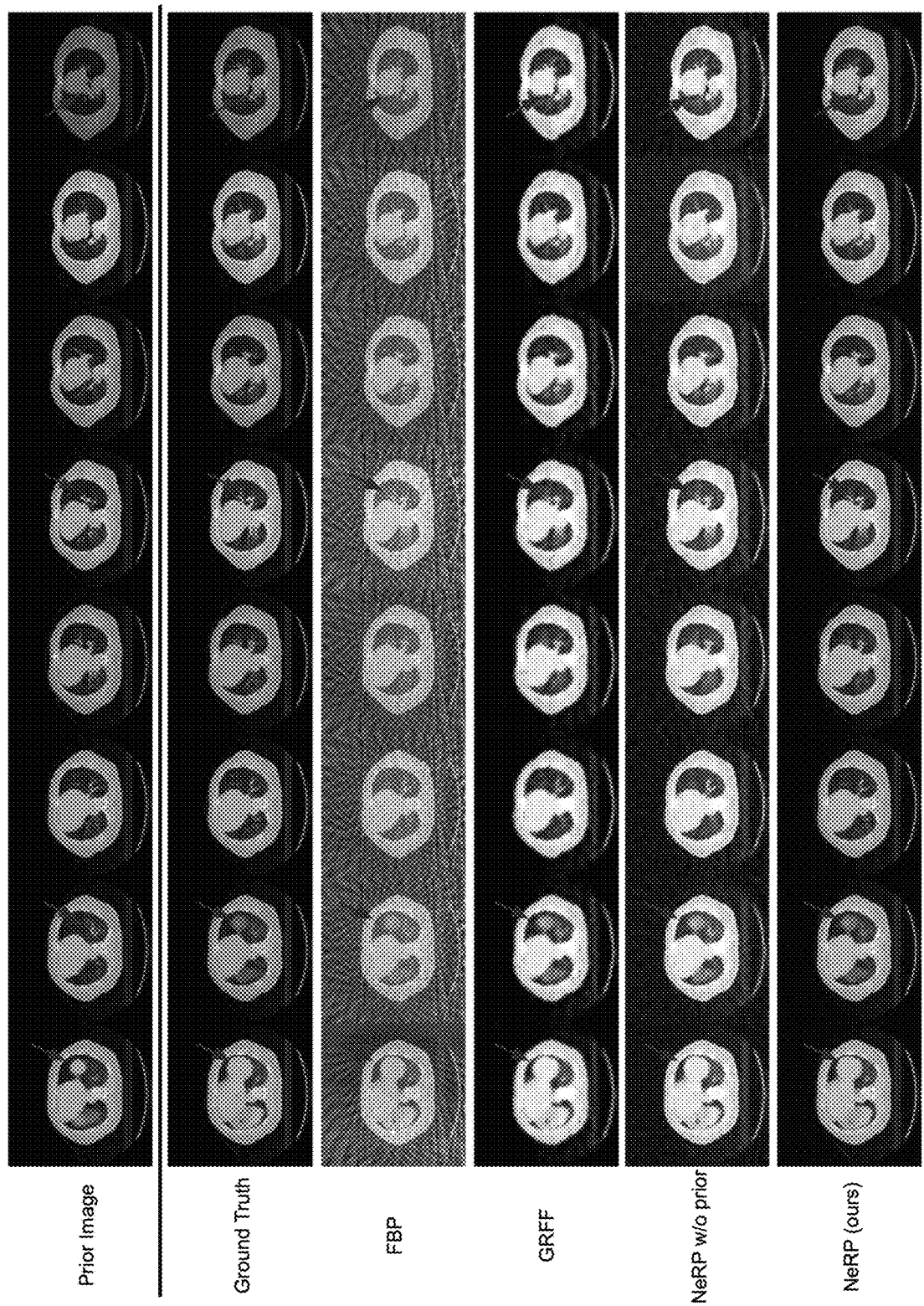
FIG. 4 is an image grid showing results of 3D CT image reconstruction for pancreas 4D CT data using 20 projections, comparing various techniques for reconstruction.

FIG. 4. Results of 3D CT image reconstruction for pancreas 4D CT data using 20 projections, where each column shows the cross-sectional image of the entire 3D volume. The first and second rows show the prior 3D CT (phase 1) and the ground truth of target 3D CT (phase 6) image, where each column demonstrates cross-sectional slices of the 3D volume. The final row shows the reconstructed 3D CT images by using the NeRP method. For comparison, the second to fourth rows show the reconstruction results of FBP method, GRFF method [20] and NeRP without using prior embedding. The final row demonstrates the reconstructed 3D volumetric image using the NeRP method. We can see that the reconstructed image captures the correct anatomic structures in the target phase, with high image quality and image contrast.

TABLE I

Results of 3D CT Image Reconstruction
Using 5/10/20 Projections on Different Anatomical Sites

| Methods | Pancreas CT | HeadNeck CT | Lung CT |
|---|---|---|---|
| Projections = 10 | | | |
| FBP | 17.95/0.461 | 23.05/0.653 | 21.49/0.597 |
| GRFF [20] | 28.07/0.855 | 29.38/0.864 | 27.80/0.835 |
| NeRP w/o prior | 28.88/0.850 | 30.40/0.858 | 30.98/0.880 |
| NeRP (ours) | 37.66/0.981 | 36.92/0.976 | 32.73/0.941 |
| Projections = 20 | | | |
| FBP | 18.23/0.610 | 23.42/0.750 | 21.74/0.717 |
| GRFF [20] | 29.27/0.893 | 32.56/0.931 | 32.75/0.935 |
| NeRP w/o prior | 32.41/0.927 | 32.59/0.920 | 32.86/0.929 |
| NeRP (ours) | 39.06/0.986 | 38.81/0.985 | 36.52/0.972 |
| Projections = 30 | | | |
| FBP | 18.31/0.650 | 23.54/0.773 | 21.83/0.7443 |
| GRFF [20] | 31.53/0.932 | 32.34/0.927 | 33.13/0.942 |
| NeRP w/o prior | 33.88/0.953 | 33.53/0.942 | 33.97/0.951 |
| NeRP (ours) | 39.65/0.987 | 39.50/0.987 | 37.66/0.980 |

Evaluation metric: PSNR/SSIM values are reported.
PSNR (dB), peak signal noise ratio; SSIM, structural similarity.

For comparison, we also conducted experiments and show the results of other in reconstruction methods. First, we show the reconstruction results for "NeRP w/o prior" as an ablative study by removing the prior embedding. Comparing the image quality, we can see that the prior embedding effectively contributes to reconstructing high-quality image with sparse sampling. Moreover, we compare with the analytic reconstruction method with filtered back projection (FBP). The back-projected operation adjoint to the cone-beam projection in the forward model can reconstruct the 3D image from the given 2D projections with filter correction. As shown in FIG. 4, FBP introduces severe streaking artifacts due to the sparsely sampling measurements. Usually, FBP method requires hundreds of sampled projections to satisfy the Shannon-Nyquist theorem, and obtain artifact-free images. However, with the implicit image priors captured from deep network and prior embedding, the NeRP can overcome this limit and achieve artifact-free high-quality images with only sparsely sampled projections. Besides, we also compare with a relevant previous work [20], which also attempts to represent medical images by network-based continuous functions. We compare with the best method reported in [20] using Gaussian random Fourier feature (GRFF) and implement the method according to the technical details in [20]. Compared with GRFF, the NeRP method uses a different network architecture, and more importantly, introduces the prior embedding for learning implicit neural representations. As shown in FIG. 4, in the same 3D CT image reconstruction task, our method obtains reconstructions with better image quality than GRFF.

Figure 5:
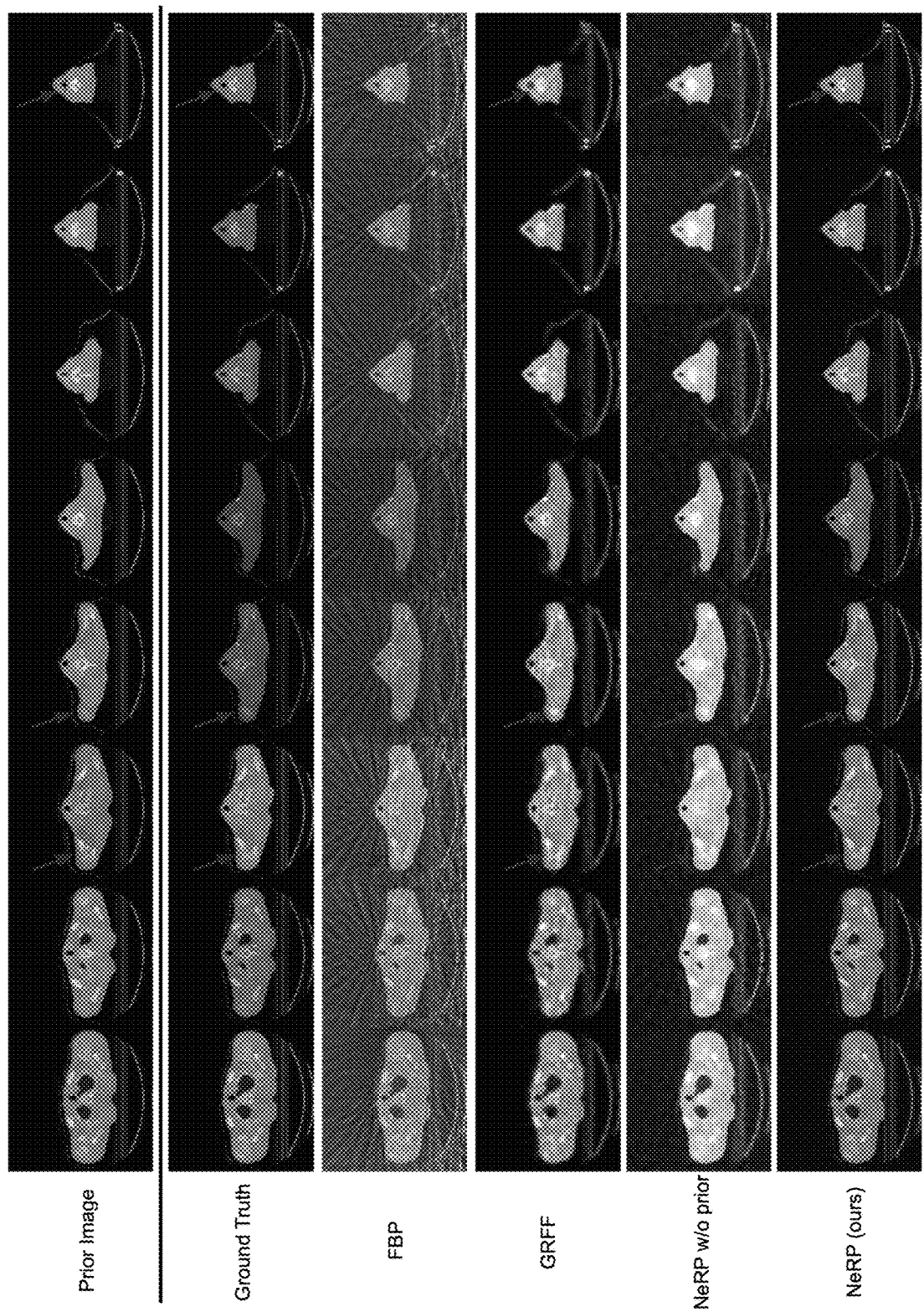
FIG. 5 is an image grid showing results of 3D CT image reconstruction for longitudinal head-and-neck CT case using 20 projections, comparing various techniques for reconstruction.

Going beyond 4D CT data, we also evaluated the clinical radiation therapy patient data with both head and neck CT and lung CT. The quantitative results for 3D CT reconstruction evaluated by PSNR and SSIM metrics are reported in Table I on different anatomic sites including pancreas CT, head and neck CT and lung CT with all comparison methods. To evaluate the effectiveness under different settings, we also compare the reconstruction results with different number of projections. The NeRP method achieves the best performance in either metric for all the 3D CT image cases with 10/20/30 projections respectively, outperforming all the other methods without using prior image embedding. Reconstructed images for longitudinal head-and-neck CT case are shown in FIG. 5. The prior image (former scan) and the ground truth target image (latter scan) are shown in the first two rows, where each column demonstrates cross-sectional slices of the 3D volume. The reconstructed 3D CT image using our NeRP method are demonstrated in the last row, which successfully captures the accurate anatomic structure and fine details different from prior image. Besides, comparing with other methods including FBP, GRFF and NeRP w/o prior, our method is able to reconstruct higher-quality images with sharper organ boundaries, higher-contrast bone regions and reduced noise and artifacts. More importantly, we show that NeRP is a general reconstruction methodology that can be applied to different body sites across different patients, as shown in these two cases for head-and-neck and lung. This demonstrates the potential capability of NeRP for practical clinical application. For comparison, the second to fourth rows show the reconstruction results of FBP method, GRFF method and NeRP without using prior embedding.

Experiments on 2D MRI Image Reconstruction

We conducted experiments to evaluate the NeRP method for MRI image reconstruction. We aimed to reconstruct 2D MRI images with sparsely sampled frequency space (k-space) data by using a radial sampling pattern for data acquisition, which is widely used in clinical MRI. The 2D NUFFT for radial sampling is used as the forward model to compute and sample k-space data as shown in FIG. 2. In addition to down-sampled k-space measurements, we also assume that a prior image from a previous scan is available. In the brain tumor regression dataset, we use the first MRI exam as the prior image to reconstruct the MRI image in the second exam. After pre-processing, 2D MRI images are all resized to 256×256.

Figure 6:
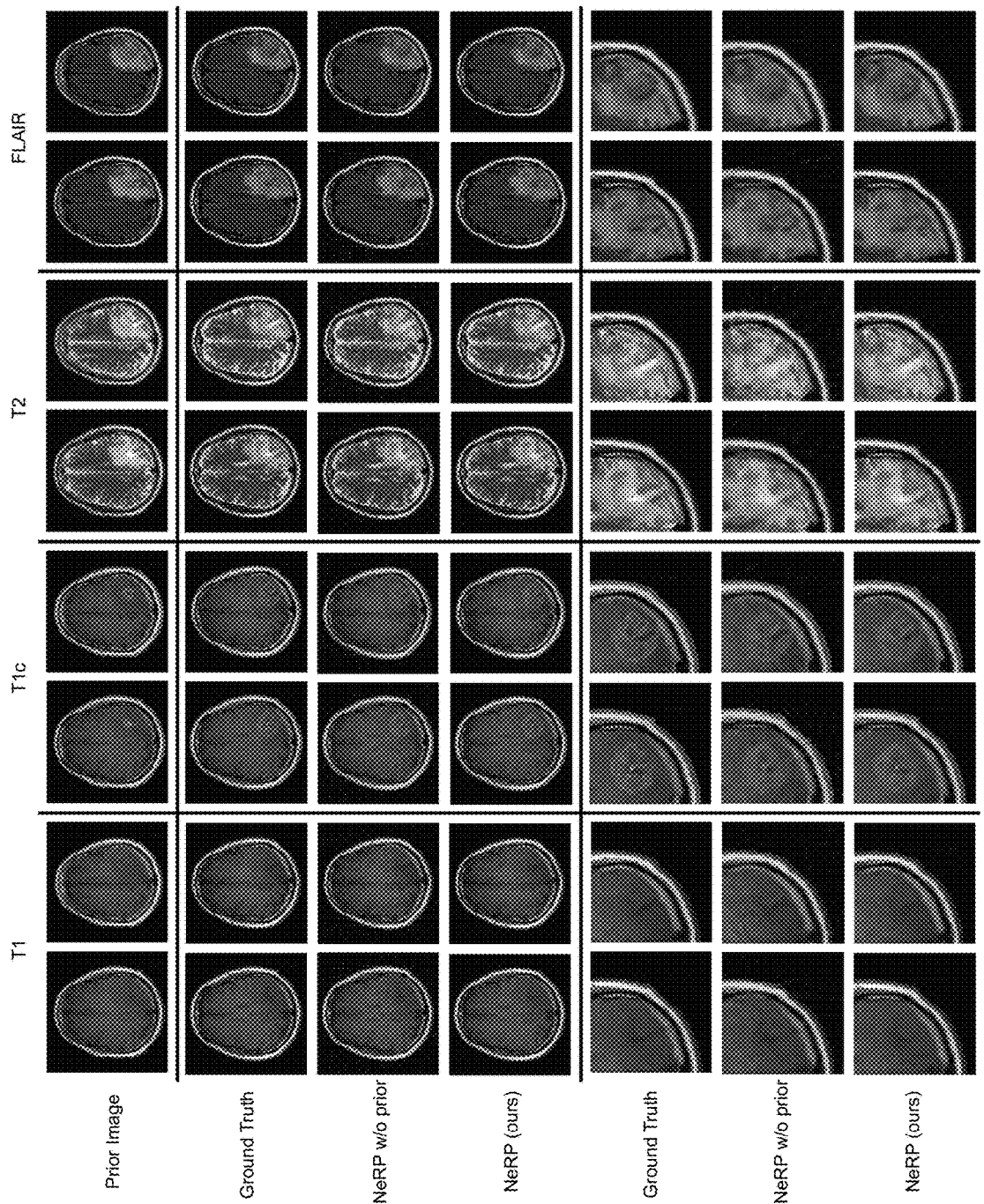
FIG. 6 is an image grid showing results of 2D MRI image reconstruction for multi-modality MRI data using 40 radial spokes, according to embodiments of the invention.

FIG. 6 demonstrates 2D MRI reconstruction results for multi-modality MR images using 40 radial spokes. The first and second rows show the prior image (the first exam) and the ground truth target image (the second exam) for one randomly selected patient with four modalities (T1, T1c, T2, FLAIR). For each modality, there are two cross-sectional 2D MRI images as two separate reconstruction cases. Comparing the prior images and target images, we can clearly see the tumor progression with the changed shape and size in these two exams. The reconstruction results for NeRP and NeRP w/o prior are shown in the third and fourth row, respectively. For better visualization and comparison, we zoom in and crop the sub-image of the corresponding tumor regions of the ground truth and reconstruction images. The last three rows show the cropped sub-images of the tumor regions corresponding to the images in the second, third, and fourth rows, respectively. From the comparison, it is seen that the reconstructed images from sparsely down-sampled k-space data can accurately capture the fine detailed structures especially in the tumor region, which is different from that in the prior image. It is clear that the prior embedding can help to reconstruct high-quality images from sparsely sampled k-space data in the second exam by efficiently exploiting prior knowledge for the same patient. More importantly, the reconstruction method can be easily generalized to different MR image modalities, which indicates the potential for other practical applications.

Experiments on 3D MRI Image Reconstruction

Using the same dataset with brain tumor regression, we further evaluated the 3D MRI image reconstruction. In this case, the entire 3D MRI volume in the first exam is used as the prior image in order to reconstruct the 3D MRI image in the second exam for the same patient. The forward model is the 3D NUFFT to compute and sample 3D k-space data. The whole learning framework of NeRP is similar to that of 2D MRI reconstruction except for using a 3D coordinate index. In pre-processing, all the 3D MRI images are cropped and resized to 128×128×24.

TABLE II

Results of 3D MRI Image Reconstruction
Using 30/40/50 Radial Spokes for Different Image Modalities

| Methods | T1 | T1c | T2 | FLAIR |
|---|---|---|---|---|
| Spokes = 30 | | | | |
| Adjoint NUFFT | 20.91/0.63 | 21.68/0.63 | 19.55/0.57 | 19.77/0.58 |
| GRFF [20] | 27.98/0.90 | 27.67/0.88 | 25.66/0.85 | 25.98/0.86 |
| NeRP w/o prior | 27.49/0.85 | 27.82/0.87 | 25.91/0.85 | 26.87/0.88 |
| NeRP (ours) | 28.43/0.90 | 29.06/0.92 | 26.86/0.90 | 27.52/0.90 |
| Spokes = 40 | | | | |
| Adjoint NUFFT | 21.30/0.66 | 22.05/0.67 | 20.17/0.62 | 20.23/0.61 |
| GRFF [20] | 28.18/0.90 | 28.11/0.89 | 25.67/0.85 | 25.99/0.86 |
| NeRP w/o prior | 29.70/0.92 | 29.29/0.91 | 27.59/0.91 | 27.54/0.90 |
| NeRP (ours) | 31.75/0.96 | 30.53/0.94 | 28.73/0.93 | 29.07/0.93 |
| Spokes = 50 | | | | |
| Adjoint NUFFT | 21.40/0.68 | 22.26/0.69 | 20.42/0.64 | 20.49/0.64 |
| GRFF [20] | 28.50/0.91 | 27.59/0.88 | 25.23/0.85 | 25.90/0.87 |
| NeRP w/o prior | 30.65/0.94 | 29.26/0.91 | 28.40/0.92 | 27.68/0.90 |
| NeRP (ours) | 32.55/0.96 | 31.37/0.95 | 30.13/0.95 | 30.02/0.94 |

Evaluation metric: PSNR/SSIM values are reported.
PSNR (dB), peak signal noise ratio; SSIM, structural similarity.

Figure 7:
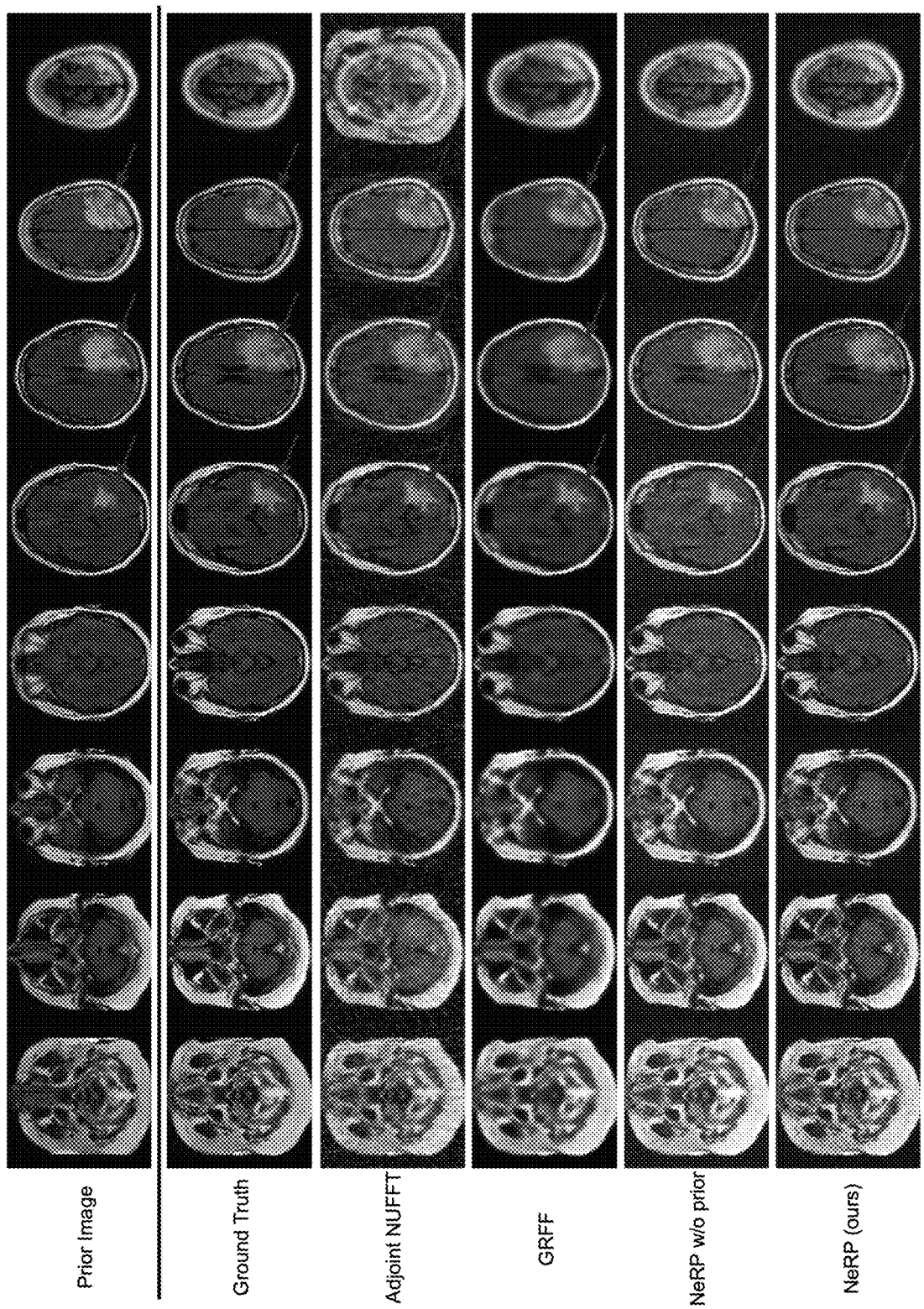
FIG. 7 is an image grid showing results of 3D MRI image reconstruction for FLAIR modality using 40 radial spokes, comparing various techniques for reconstruction.
Figures 8A, 8B:
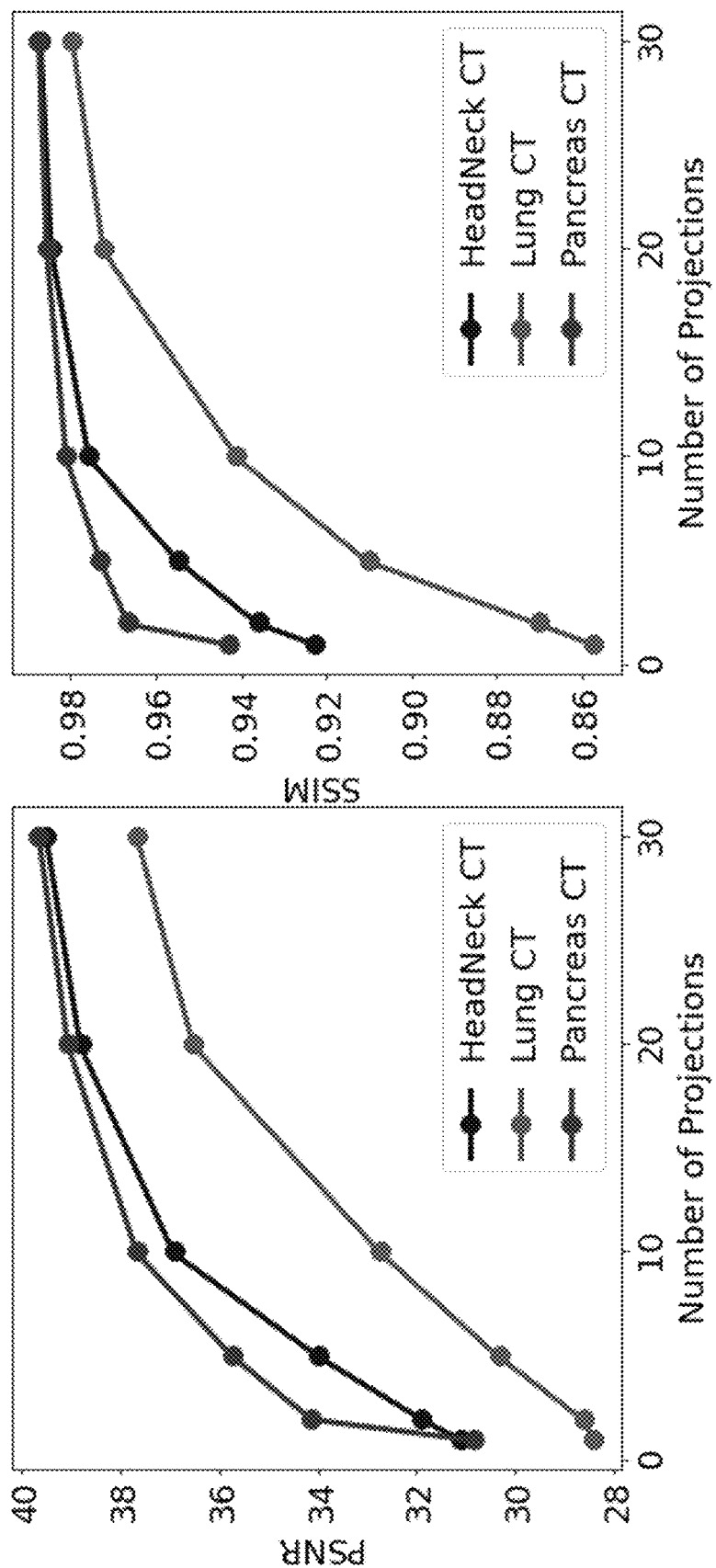
FIGS. 8A-8B are graphs showing results of 3D CT image reconstruction (PSNR and SSIM, respectively) with different number of sampled projections.
Figures 9A, 9B:
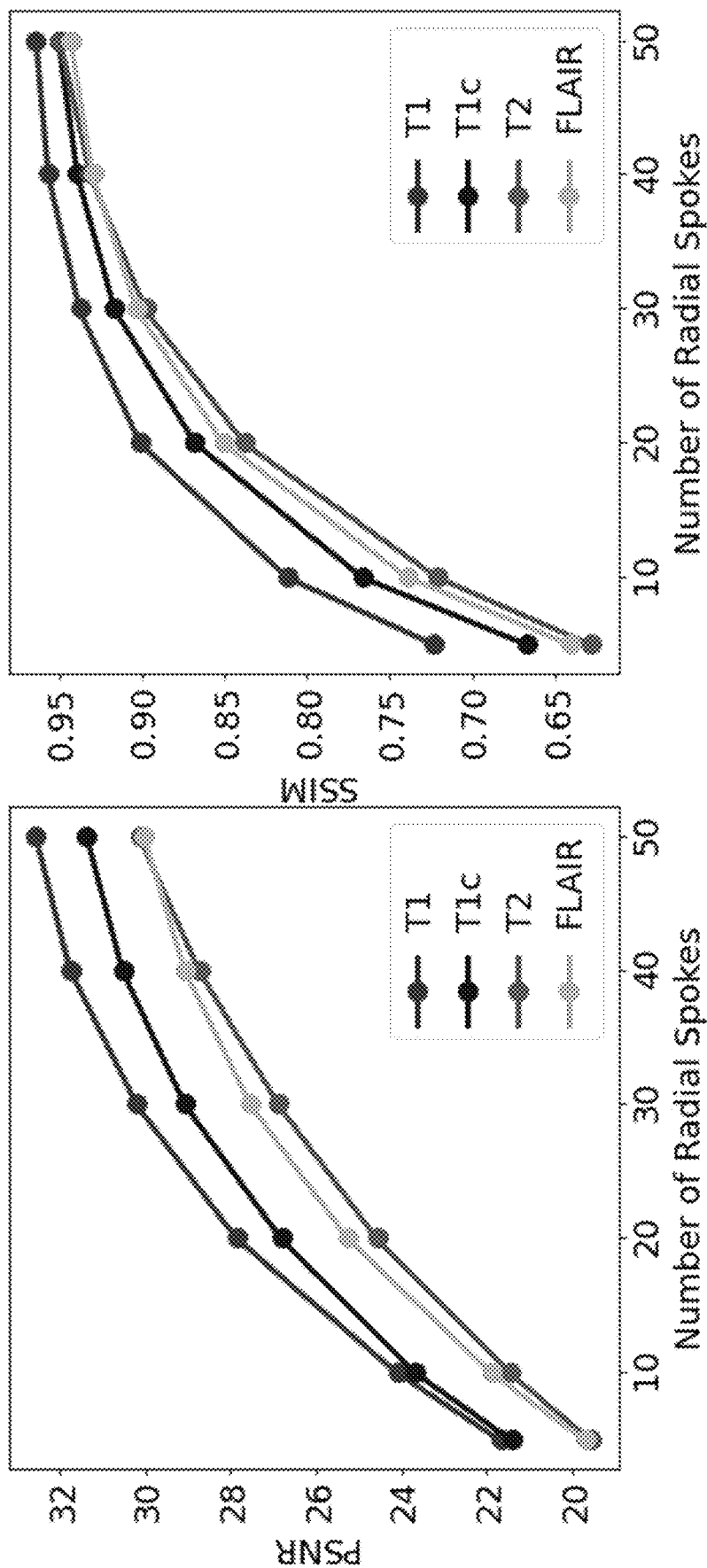
FIGS. 9A-9B are graphs showing results of 3D MRI image reconstruction (PSNR and SSIM, respectively) with different number of sampled radial spokes.

Quantitative results of 3D MRI image reconstruction evaluated by PSNR and SSIM metrics are reported in Table II for different image modalities including T1, T1c, T2 and FLAIR. We compare the results of different reconstruction methods with 30/40/50 sampled radial spokes, respectively. From the Table II, our NeRP method achieves better performance than other methods without using prior image for all the image modalities. Reconstructed 3D MRI images for FLAIR modality using 40 radial spokes are demonstrated in FIG. 7. The first and second rows show the prior 3D MRI (first exam) and ground truth of target 3D MRI (second exam) image, where each column demonstrates cross-sectional slices of the 3D volume. The final row shows the reconstructed 3D MRI images from the NeRP method. The reconstruction results indicate that our method is able to reconstruct the precise changes in brain tumor region even with sparsely sampled k-space data, which is crucial for clinical diagnosis and cancer treatment. Moreover, for comparison, we also use an analytic reconstruction method with the Adjoint NUFFT operator to recover the data in image space with density compensation. We can see the reconstructed images using adjoint NUFFT have severe streaking artifacts due to the sparse down-sampling of k-space data. In addition, we also compare with GRFF method and NeRP w/o prior as ablative study. The comparison shows that our method can not only reconstruct more accurate tumor structures, but also achieves better image quality such as sharper anatomic boundaries and higher soft tissue contrast. All of these results demonstrate the effectiveness and superiority of the NeRP method for 3D MRI image reconstruction.

Analysis of Network Structure

For the NeRP method, one important issue is to set a proper network structure for the MLP backbone. The MLP network parameters serve as the variables to expand the function space for network optimization and seeking the optimal reconstructed images. The number of network parameters is related to the depth and width of the MLP, i.e., the number of layers and the number of neurons in each layer. To analyze the influence of network structures, we conduct ablation study to obtain the reconstruction results with changed MLP depth and width as shown in Table III. Here, the 3D pancreas CT image is reconstructed from 20 projections while the 3D T1 MRI image is reconstructed from 40 radial spokes. From Table III, we see that the reconstruction results are not very sensitive to the change of network depth or width, which indicates the NeRP method is robust to the specific choice of network structure. In experiments, we also observe that training the MLP model could be more difficult with more layers, where the insufficient optimization may cause worse reconstruction results.

Analysis of Sparse Sampling Ratio

To better analyze the influence of sparse sampling ratio, we use NeRP to reconstruct 3D CT and MRI images with different number of sampled projections or radial spokes. FIGS. 8A-8B and FIGS. 9A-9B show the PSNR and SSIM of reconstructed CT and MRI images with increasing sampling, respectively. The curves show that more samples in measurements field can always reconstruct more precise structures with better image quality. For CT images, sampling around 20 projections reaches the plateau when using NeRP reconstruction method, while around 40 sampled radial spokes are required for MRI image reconstruction to achieve the best image quality. The analysis gives the guidance for designing sensor acquisition in imaging system when using NeRP method for image reconstruction.

TABLE III

Analysis of Network Structure
for 3D CT/MRI Image Reconstruction

| Network Structure | | Pancreas CT | T1 MRI |
|---|---|---|---|
| Width = 512 | 4 Layers | 38.04/0.981 | 29.93/0.933 |
| | 6 Layers | 38.83/0.984 | 31.23/0.950 |
| | 8 Layers | 37.44/0.977 | 31.75/0.956 |
| Width = 256 | 8 Layers | 39.06/0.986 | 31.10/0.948 |
| | 16 Layers | 34.04/0.953 | 30.98/0.945 |
| | 20 Layers | 34.04/0.955 | 30.23/0.937 |

Evaluation metric: PSNR/SSIM values are reported.
PSNR (dB), peak signal noise ratio; SSIM, structural similarity.

In summary, herein is disclosed a deep learning-based medical image reconstruction methodology by learning implicit neural representations with prior embedding (NeRP), which efficiently incorporates the prior knowledge and learns to reconstruct the target image through implicit neural representations. Through the experiments for 2D/3D MRI and CT image reconstruction, we show that the NeRP method is able to provide high-quality reconstruction images even with sparsely sampled measurements data. The NeRP approach possesses a number of unique advantages: (1) requires no training data from external subjects for developing networks; (2) accurate reconstruction of small and detailed changes in such as anatomic structure or tumor progression; (3) broad applicability to different body sites, different imaging modalities and different patients. For medical images, it is common that a patient is scanned multiple times for clinical diagnosis or treatment follow-up, for the purpose of treatment planning or monitoring of the changes in tumor volume before and after therapy. In a longitudinal image series, previous scans can provide useful prior knowledge for NeRP image reconstruction. The effectiveness of NeRP and advantages of prior embedding have been demonstrated in the extensive experiments.

The invention claimed is:

1. A method for diagnostic imaging reconstruction comprising:

storing a prior image $x^{pr}$ from a scan of a subject, comprising image intensity at each coordinate in image space;

initializing parameters of a neural network using the prior image $x^{pr}$;

wherein the neural network maps coordinates in image space to corresponding intensity values in the prior image;

wherein initializing the parameters comprises minimizing an objective function representing a difference between intensity values of the prior image and predicted intensity values output from the neural network, thereby creating an implicit neural representation of the prior image;

performing a scan to acquire subsampled (sparse) measurements y of the subject;

training the neural network using the measurements y to learn a neural representation of a reconstructed image x, wherein the training comprises minimizing an objective function representing a difference between the measurements y and a forward model applied to predicted image intensity values output from the neural network;

computing image intensity values output from the trained neural network from coordinates in image space input to the trained neural network to produce predicted image intensity values.

2. The method of claim 1 wherein Fourier feature mapping is used to transform spatial coordinates to encoded coordinates prior to input to the neural network.

3. The method of claim 1 wherein the neural network is implemented by a deep fully-connected network or multi-layer perceptron (MLP).

4. The method of claim 1 wherein the MLP uses periodic activation functions after each fully-connected layer.

5. The method of claim 1 wherein performing a scan to acquire subsampled (sparse) measurements y of the subject comprises performing an MRI scan to acquire the subsampled (sparse) measurements y of the subject.

6. The method of claim 1 wherein performing a scan to acquire subsampled (sparse) measurements y of the subject comprises performing an CT scan to acquire the subsampled (sparse) measurements y of the subject.

* * * * *